(12) United States Patent
Lawner et al.

(10) Patent No.: US 8,177,552 B1
(45) Date of Patent: May 15, 2012

(54) ELASTIC BANDS FOR ORTHODONTIC USE

(76) Inventors: Neil O. Lawner, New York, NY (US); Marsha Blanke, West Patterson, NJ (US)

( * ) Notice: Subject to any disclaimer, the term of this patent is extended or adjusted under 35 U.S.C. 154(b) by 0 days.

(21) Appl. No.: 13/069,698

(22) Filed: Mar. 23, 2011

(51) Int. Cl.
*A61C 3/00* (2006.01)

(52) U.S. Cl. ......................................................... 433/24

(58) Field of Classification Search .............. 433/2, 18, 433/19, 10, 11, 15, 13, 23, 24; 206/805; 132/321
See application file for complete search history.

(56) References Cited

U.S. PATENT DOCUMENTS

| | | | |
|---|---|---|---|
| 3,593,421 A | 7/1971 | Brader | |
| 3,758,947 A | 9/1973 | Kesling | |
| 4,054,997 A | 10/1977 | Wallshein | |
| 5,378,146 A | 1/1995 | Sterrett | |
| 5,674,067 A * | 10/1997 | Masel | 433/24 |
| 5,829,974 A | 11/1998 | Brosius | |
| 5,878,945 A | 3/1999 | Weder | |
| 6,280,186 B1 | 8/2001 | Logan | |
| 6,935,858 B2 | 8/2005 | Cleary | |
| 7,445,447 B2 | 11/2008 | Hekimian | |
| 2008/0153052 A1 | 6/2008 | Ianieri | |

OTHER PUBLICATIONS

Silly Bandz archive document from www.sillybandz.com on Aug. 12, 2010 and May 2, 2009.*
Silly Bandz archive document from www.sillybandz.com on Aug. 12, 2010 and May 2009.*
Silly Bandz advertisement 2010.

* cited by examiner

*Primary Examiner* — Cris L Rodriguez
*Assistant Examiner* — Mirayda A Aponte
(74) *Attorney, Agent, or Firm* — Connolly Bove Lodge & Hutz

(57) ABSTRACT

An orthodontic band is provided made from an elastomeric material wherein the band has a shape which simulates the profile of an object with an open area within the band. In its unstretched condition the outer perimeter of the band is of a shape which is not a smooth continuous endless curve to thereby simulate the profile of the object, such as a star or heart. The band is mounted to a bracket on an upper tooth and to a bracket on a lower tooth by stretching the band and looping the open area over hooks on both brackets. The stretched band thereby provides a force against the teeth.

5 Claims, 5 Drawing Sheets

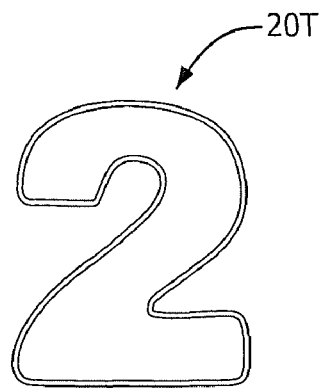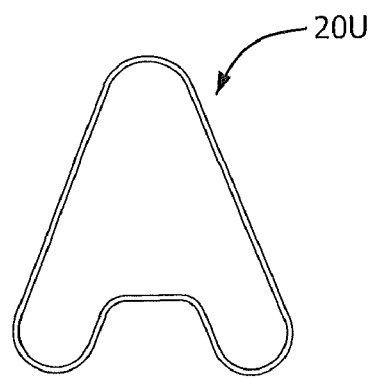
FIG. 20  FIG. 21
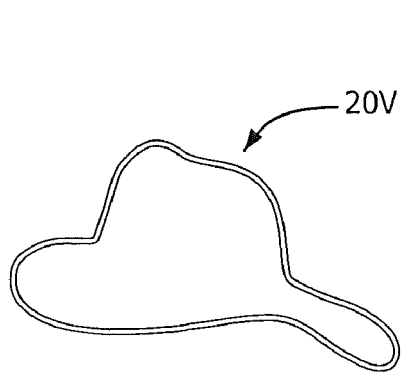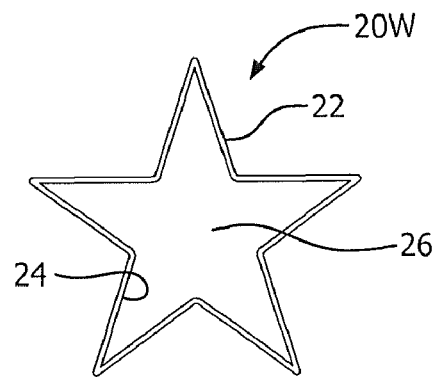
FIG. 22  FIG. 23
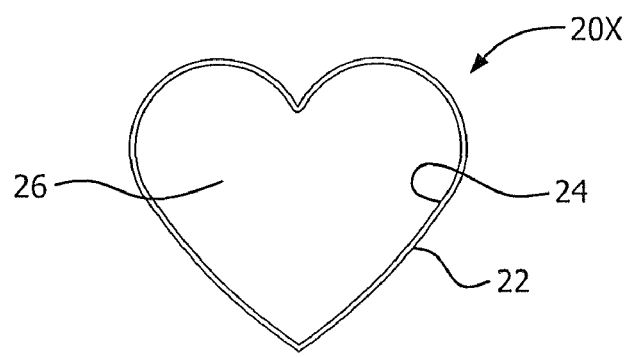
FIG. 24

ELASTIC BANDS FOR ORTHODONTIC USE

BACKGROUND OF THE INVENTION

Various orthodontic treatments include the use of an elastic band which would be hooked to a bracket on the tooth of one jaw and to a further bracket on the tooth of another jaw. For example, where the band is hooked to a front tooth on the upper jaw and to a back tooth on the lower jaw the front tooth would be moved backwards or inwardly. Most patients who use such orthodontic procedure are children. In order to encourage the child patient to use such orthodontic procedures it would be desirable if the elastic band could be formed in such a manner that would find some attractiveness to the child to encourage cooperativeness and lessen any degree of resistance to using such orthodontic treatments.

SUMMARY OF THE INVENTION

An object of this invention is to provide an elastic band for use in orthodontic procedures.

A further object of this invention is to provide such an elastic band which would be readily pleasing to a child patient.

In accordance with this invention the elastic band simulates in its outer perimeter the profile of a recognizable object that would be pleasing to a child patient. The inner perimeter would define an open space so that the elastic band could be stretched and hooked over a bracket on an upper tooth and a bracket on a lower tooth. In this stretched condition the open shape becomes a smooth endless loop of elongated elliptical form. When in its unstretched condition, however, the band forms the profile of the recognizable object. Preferably the object is a star or a heart.

THE DRAWINGS

FIG. 20 is a front elevational view of a band in the form of a number in accordance with this invention;

FIG. 21 is a front elevational view of a band in the form of a letter in accordance with this invention;

FIG. 22 is a front elevational view of a band in the form of a fireman's hat in accordance with this invention;

FIG. 23 is a front elevational view of a band in the form of a star in accordance with this invention;

FIG. 24 is a front elevational view of a band in the form of a heart in accordance with this invention.

DETAILED DESCRIPTION

Figure 1:
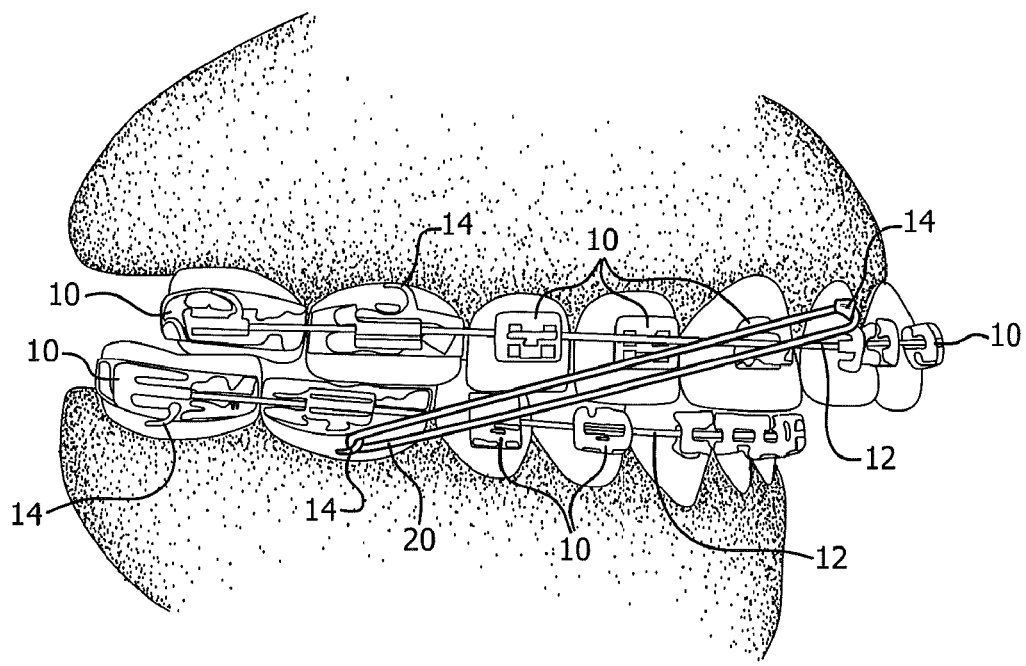
FIG. 1 is a front elevational view showing the pertinent portions in the mouth of a patient which would incorporate an elastic band in the orthodontic procedure in accordance with this invention.
Figure 25:
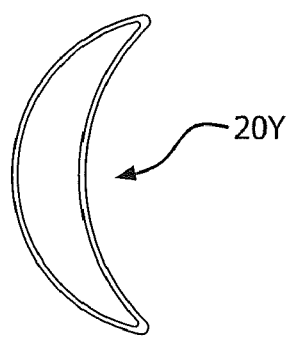
FIG. 25 is a front elevational view of a band in the form of a crescent in accordance with this invention.

The present invention relates to the use of elastic bands in various intraoral orthodontic procedures. FIG. 1 illustrates a typical procedure wherein a bracket 10 is mounted to each tooth on the upper and lower jaws. The brackets 10 may be used for mounting an arch wire 12 to each jaw. At least some of the brackets 10 include a hook 14. The present invention is directed to intraoral orthodontic procedures which utilize an elastic band 20 that would be stretched and looped around a hook 14 on the bracket of an upper tooth and a hook 14 on the bracket of a lower tooth. In the orthodontic procedure illustrated in FIG. 1 the upper tooth is a front tooth while the lower tooth is a back tooth. The resiliency of the elastic band creates a traction force that would tend to move the upper tooth backwardly as part of the orthodontic procedure.

As illustrated in its use condition the elastic band 20 forms a generally oval or elliptical continuous loop.

In the conventional practice of such orthodontic procedures the elastic bands, in their unstretched condition, are of smooth continuous loop form, such as an ellipse or circle. The present invention is directed to modification of the elastic band that would result in the band being more attractive to a patient, particularly a child patient, so as to lessen any resistance from and promote patient cooperation and compliance in orthodontic treatment.

In general, the elastic band would be made of conventional orthodontic elastic band materials, such as being formed from a suitable latex or other elastic type material having the desired elastic properties to provide the sufficient resiliency of achieving the necessary traction force needed for the orthodontic treatment. Such orthodontic treatment could involve movement of malpositioned teeth to correct locations along the dental arch and thereby improve occlusion as well as providing a more pleasing aesthetic appearance. As illustrated in FIG. 1 the malocclusion would be corrected by urging the upper dental arch rearwardly.

In accordance with this invention the elastic band in its unstretched condition has an outer perimeter which simulates the profile of a recognizable object. Preferably the band is of uniform width and thickness whereby the inner perimeter defines an open area which would be parallel to the outer perimeter in simulating the profile of the object. In use, however, the band would be looped over a hook on each of an upper tooth and a lower tooth as generally illustrated by the band 20 of FIG. 1. In order to be looped over both hooks of the two brackets the band would be stretched and the open area would form a smooth continuous elliptical shape. The outer perimeter would also form such elliptical shape. Upon being removed from the brackets, the band then tends to return toward its original unstretched shape which again simulates the profile of the object.

In a broad aspect of this invention, the elastic bands 20 could be manufactured in various geometric, animal, botanical, numerical, celestial, or other recognizable shapes in their unstretched condition. While in such unstretched condition, the bands would motivate a patient to use them regularly and thereby promote the movement of teeth during orthodontic treatment in a more efficient manner. In their stretched condition, when applied during orthodontic treatment, the elastic bands would not exhibit such recognizable shape, but would revert to an elliptical stretched elastic shape.

Various types of recognizable objects or shapes may be simulated in accordance with this invention. There is presently being marketed elastic bands to be worn by, for example, children as bracelets or wrist bands. One such form of elastic bands being marketed in this manner is known as SILLY BANDZ. Such commercial bracelet type bands are merely examples of some of the shapes or objects that could be used in accordance with this invention. A characteristic of the shape is that its outer perimeter simulates the profile of an object that is not a smooth continuous curve. FIGS. 2-24 and the following description are directed to just some of the shapes or objects which meet the criteria of this invention.

Figure 2:
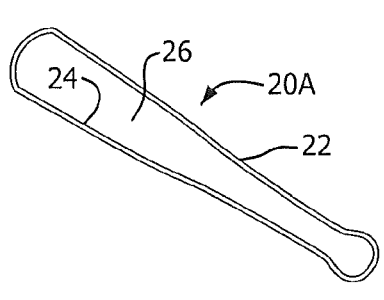
FIG. 2 is a front elevational view of a band in the form of a baseball bat in accordance with this invention.

FIG. 2 illustrates a band 20A. As shown therein the outer perimeter 22 simulates an object which is a baseball bat. The inner perimeter 24 defines an open area 26. In use the band would be stretched from the unstretched condition shown in FIG. 2 so that one end of the simulated baseball bat would be looped over a hook on one bracket and the other end of the simulated baseball bat would be looped over a hook on the other bracket. In this stretched condition the common open area 26 results in the inner perimeter 24 taking a shape which is of smooth continuous elliptical form as illustrated by the band 20 in FIG. 1. The outer perimeter 22 would also take such form. When detached from the bracket the band 20A would again assume the form of an object which is the profile of a baseball bat.

FIGS. 23 and 24 illustrate preferred practices of this invention. As shown in FIG. 23 the band 20W is in the shape of a star, while FIG. 24 shows the band 20X in the shape of a heart. In both of these versions the shape is defined by the outer perimeter 22 which is a profile that is not a smooth continuous endless curve. The inner perimeter 24 is parallel to outer perimeter 22 and circumscribes a single completely open area 26.

The following are examples of different types of recognizable objects or shapes which may be simulated by the elastic band of this invention.

Figure 11:
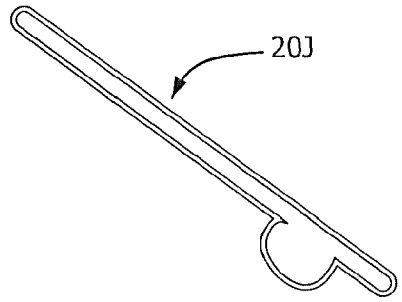
FIG. 11 is a front elevational view of a band in the form of a fishing rod in accordance with this invention.
Figure 12:
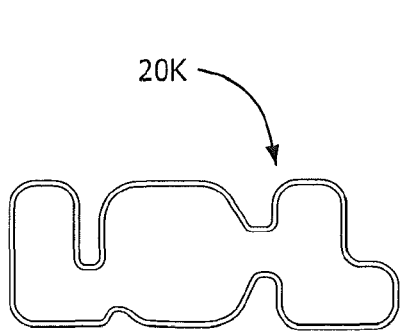
FIG. 12 is a front elevational view of a band in the form of an LOL text designation in accordance with this invention.

One form of object may be generally considered as an entertainment object which could include sports equipment such as the baseball bat 20A of FIG. 2. FIG. 11 illustrates a further form of entertainment with the object of band 20J being a fishing rod. Thus, such entertainment objects could be sports related which could include simulated sports clothing such as a baseball cap or glove or shoes, as well as baseball equipment including homeplate. A baseball, however, would not be included unless the stitches of the ball are prominent. In that regard, the outer profile is an object which is not a smooth continuous endless curve. This differentiates the object from conventional smooth continuous endless curve bands which have no special appeal to child patients. The entertainment type objects which are sports related could include objects from other sports, such as football, basketball, hockey, track, etc. as well as associated sports objects including megaphones, cheerleaders, flags, etc. Various hunting and fishing equipment could include guns, fishing rods, boats and other known hunting and fishing equipment. Similarly, any of the recognizable objects used in sports and various forms of entertainment could also be used, provided these objects meet the criteria of the outer profile being of a shape which is not a smooth continuous endless curve and wherein an open area is provided within the perimeter so that the same open area can be looped over the hooks on the brackets.

Figure 3:
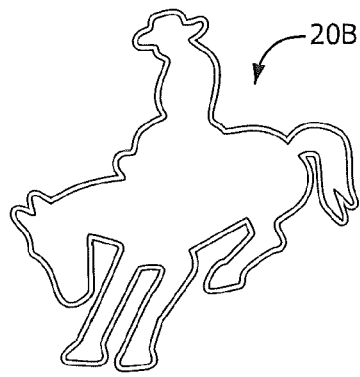
FIG. 3 is a front elevational view of a band in the form of a cowboy riding a horse in accordance with this invention.

A further group of exemplary objects could be people or recognizable objects associated with the occupations of people. FIG. 3, for example, illustrates a cowboy or western theme object where band 20B is a simulation of a cowboy riding a horse. FIG. 22 illustrates a fireman's hat being simulated by band 20V. Various athletes, including those in their occupational equipment, such as football players, would also be considered as part of the people or occupations in such simulated objects. Further, people such as ballerinas or dancers would also be examples of such simulated people/occupations objects.

Figure 4:
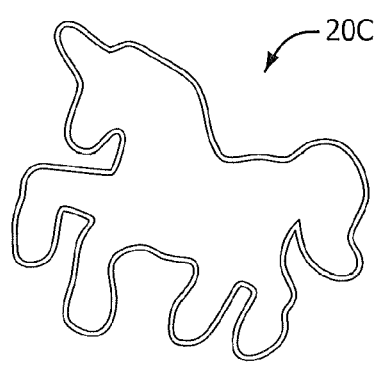
FIG. 4 is a front elevational view of a band in the form of a unicorn in accordance with this invention.
Figure 10:
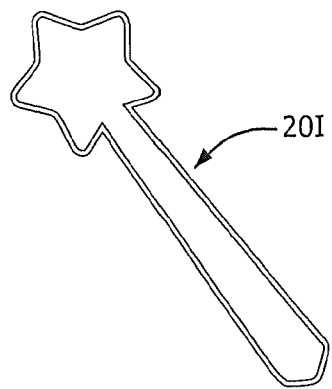
FIG. 10 is a front elevational view of a band in the form of a wand in accordance with this invention.
Figure 16:
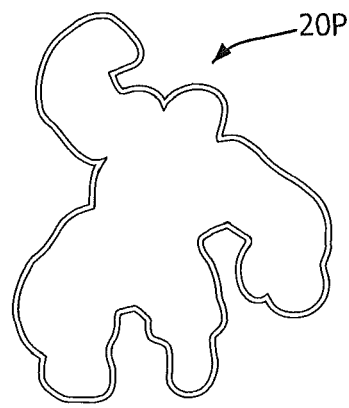
FIG. 16 is a front elevational view of a band in the form of a superhero in accordance with this invention.

A further group of objects might be considered as fantasy objects. FIG. 4, for example, shows a band 20C which is a simulated unicorn. FIG. 10 shows a band 20I where the object is a simulated wand. FIG. 16 illustrates a band 20P which is a simulated superhero. Other exemplary fantasy objects could include mermaids, fairies, dragons, phoenix and genies. Such objects may include mystical objects, such as witches, wizards and flaming dragons. Further fantasy objects could include robots, as well as various superheroes, including comic book or television type superheroes.

Figure 5:
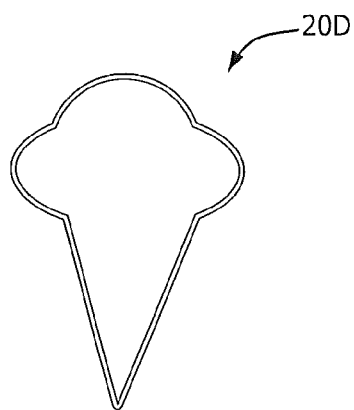
FIG. 5 is a front elevational view of a band in the form of an ice cream cone in accordance with this invention.

A further example of a group of simulated objects is illustrated in FIG. 5 where the band 20D is an ice cream cone, thus simulating a food object. The band may take the shape of any other recognizable food item, including drinks, hot dogs and other types of food having recognizable profiles.

Figure 6:
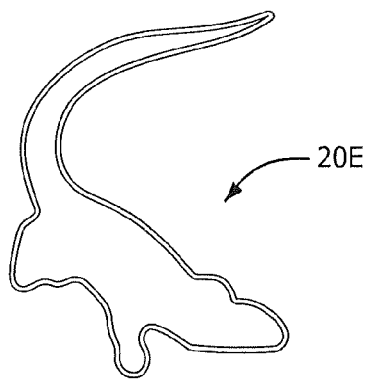
FIG. 6 is a front elevational view of a band in the form of a reptile in accordance with this invention.
Figure 7:
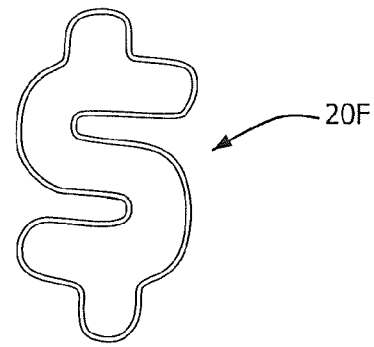
FIG. 7 is a front elevational view of a band in the form of a dollar sign in accordance with this invention.
Figure 13:
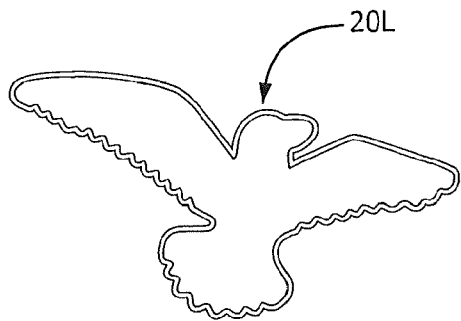
FIG. 13 is a front elevational view of a band in the form of an American Eagle in accordance with this invention.
Figure 14:
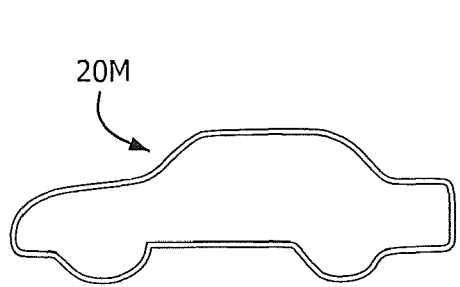
FIG. 14 is a front elevational view of a band in the form of a vehicle in accordance with this invention.
Figure 15:
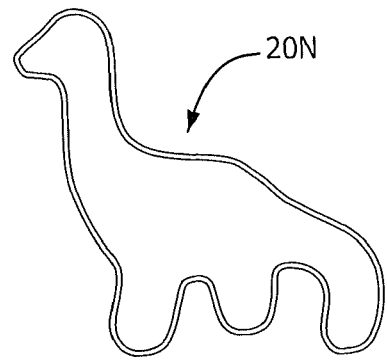
FIG. 15 is a front elevational view of a band in the form of a dinosaur in accordance with this invention.
Figure 17:
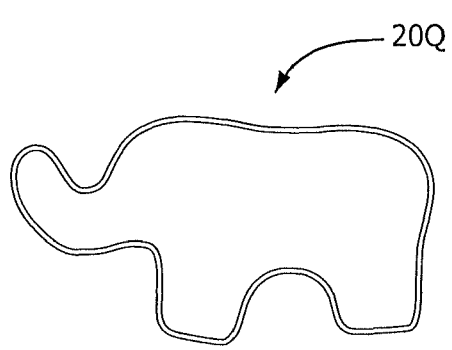
FIG. 17 is a front elevational view of a band in the form of an elephant in accordance with this invention.
Figure 18:
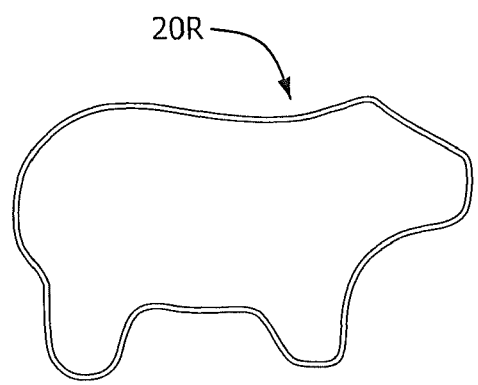
FIG. 18 is a front elevational view of a band in the form of a farm animal in accordance with this invention.

A further form of group of objects that could be simulated would be living objects such as animals and plants. FIG. 6 shows a band 20E in the form of a reptile. FIG. 13 shows an eagle, representative of a bird for the band 20L. FIG. 15 exemplifies a band 20N which is a prehistoric animal, namely a dinosaur. FIG. 17 shows a band 20Q which would represent a wild animal or zoo animal, such as an elephant, while FIG. 18 shows a band 20R representing a farm animal. Various types of dinosaurs or prehistoric animals, as well as farm animals, zoo animals, wild animals, birds, fish and various types of plants might be included in the simulated living objects group as the object being simulated.

Figure 9:
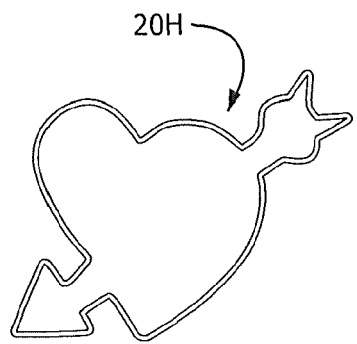
FIG. 9 is a front elevational view of a band in the form of an arrow shot through the heart in accordance with this invention.

A further group of objects could be fun objects. Such fun shapes could be a heart (FIG. 24), a star (FIG. 23) or even a simulated dollar sign, such as band 20F of FIG. 7. FIG. 9 illustrates a band 20H which would be a fun shape depicting "love" where an arrow is shot through the heart. Other fun shapes could include the sun with its projecting rays, bones, crescents and other fun type objects.

A further group of objects could be considered as generally writing/decorating communication objects. Examples of these include the texting designation LOL shown as band 20K. This group of objects may also include alphanumeric objects, such as the number illustrated by band 20T of FIG. 20 or the letter illustrated by band 20U of FIG. 21. It is to be noted that such alphanumeric objects must meet the criteria of the profile being of a shape which is not a smooth continuous endless curve. Thus, the letter "O" and the number zero, as normally made, would not be a practice of the invention. Within this category of objects could be art supplies, such as easels and brushes, as well as typewriters, telephones and computers, in addition to other common texting symbols.

A further example of simulated objects is various forms of transportation such as vehicles. The band 20M illustrated in FIG. 14 would be such an object. In addition, trains, planes, automobiles, trucks, wagons, bicycles, etc. would also be examples of such transportation objects.

Figure 8:
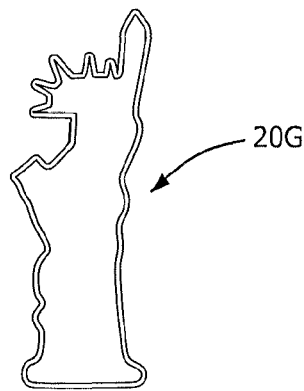
FIG. 8 is a front elevational view of a band in the form of the Statue of Liberty in accordance with this invention.
Figure 19:
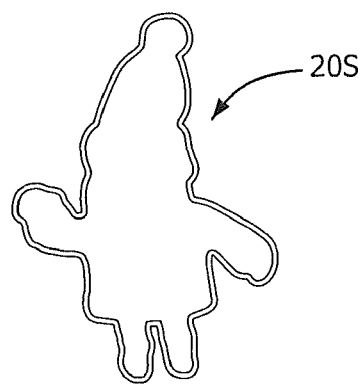
FIG. 19 is a front elevational view of a band in the form of Santa Claus in accordance with this invention.

A further group of objects could include holiday figures or various patriotic objects. FIG. 8, for example, illustrates a patriotic object where the band 20G simulates the Statue of Liberty. FIG. 13 might also be considered a patriotic object where the band 20L is an American Eagle. A holiday object is shown in FIG. 19 where the band 20S represents Santa Claus. Other patriotic objects could include a map of the United States, a depiction of the Liberty Bell and other known patriotic symbols. Holiday objects could include reindeer, Easter bunnies, Christmas trees, elves, candles and other recognizable symbols of different holidays.

A further group of simulated objects could be military objects, such as tanks, planes and various types of military ground vehicles. The vehicle 20M in FIG. 14 might be considered as a military vehicles when used for such purpose.

Yet another group of recognizable objects could broadly be considered as wearing apparel/clothing. The fireman's hat shown as band 20V in FIG. 22 is an article of clothing. This group could also include jewelry as a form of wearing apparel or clothing.

As previously pointed out, conventional orthodontic elastic bands, in their unstretched condition are of smooth continuous loop form, such as an ellipse or circle. Since the perimeter of the bands of this invention have a shape, in the unstretched condition, which is not a smooth continuous loop form, such shape would be non-circular and non-elliptical.

It is to be understood that the above description of specific types of objects, including those illustrated in the drawings, are intended to be representative of the types of recognizable objects that could be simulated for the various elastic orthodontic bands of this invention. The invention is intended to also cover any recognizable object which is characterized by having its outer perimeter simulate the profile of an object having a shape which is not a smooth continuous endless curve. Other examples of such objects could be structures, buildings, astronomic, celestial, musical and geometric shapes.

In accordance with another aspect of this invention the use of different shapes provides the orthodontist with the ability to distinguish one size band from another. Thus, the bands could be supplied as part of a kit wherein the kit would include plural sets of different shapes with the shapes of one set differing in size with regard to the size of the open space of one set from another. Thus each size would have a distinctive shape. Additionally, different colors may be used to differentiate one size from the other instead of or in addition to the use of different shapes. As should be apparent the present invention which utilizes elastic bands made of conventional latex or other type elastic material promotes patient cooperation and compliance in orthodontic treatment by providing a shape which a patient, particularly a child patient, would find to be entertaining or pleasing.

What is claimed:

1. In a method of intraorally treating a patient wherein an elastomeric continuous orthodontic band is looped around an anchor point on the upper jaw and around an anchor point on the lower jaw to cause relative movement of an upper tooth and a lower tooth, the improvement being in
    (a) providing a plurality of sets of bands each of which has the characteristics of (1) an outer perimeter simulating the profile of an object with an open area within the perimeter and (2) being made of a resilient elastic material capable of being stretched and capable of tending to return toward its unstretched shape and (3) the outer perimeter in its unstretched condition being of a shape which is non-circular and non-elliptical and which is not a smooth continuous endless curve to thereby simulate the profile of the object; the sets of bands differing from each other in size and shape with each shape corresponding to a specific size,
    (b) selecting the desired size band from the sets based on the shape of the band,
    (c) stretching the band,
    (d) mounting the band on an anchor point on the upper jaw and an anchor point on the lower jaw by looping the open area within the perimeter around the upper jaw anchor point and around the lower jaw anchor point, and
    (e) forming the open area within the perimeter into a continuous smooth endless curve when the band is mounted to the anchor points in the stretched condition of the band.

2. The method of claim 1 wherein the sets of different size bands also differ from each other in color with each color corresponding to a specific size.

3. The method of claim 1 wherein one set of bands is star shaped.

4. The method of claim 1 wherein one set of bands is heart shaped.

5. The method of claim 1 wherein one set of bands is crescent shaped.

* * * * *